US00PP29516P2

(12) United States Plant Patent
Snijder

(10) Patent No.: US PP29,516 P2
(45) Date of Patent: Jul. 17, 2018

(54) POINSETTIA PLANT NAMED 'EURZ0005'

(50) Latin Name: *Euphorbia pulcherrima*
Varietal Denomination: EURZ0005

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,563

(22) Filed: Jun. 28, 2017

(51) Int. Cl.
*A01H 5/02* (2018.01)

(52) U.S. Cl.
USPC ..... Plt./307

(58) Field of Classification Search
USPC ..... Plt./307
See application file for complete search history.

(56) References Cited

PUBLICATIONS

PLUTO Plant Variety Database Mar. 17, 2018. p. 1.*

* cited by examiner

*Primary Examiner* — Annette H Para
(74) *Attorney, Agent, or Firm* — Dale Skalla

(57) ABSTRACT

A new Poinsettia plant named 'EURZ0005' particularly distinguished by bright bluish red bract color, relatively large inflorescences with slightly serrated bracts a little upright directed, dark green foliage, early flowering response, and medium vigor.

1 Drawing Sheet

Latin name of the genus and species of the plant claimed: *Euphorbia pulcherrima.*

Varietal denomination: 'EURZ0005'.

BACKGROUND OF THE NEW PLANT

The present invention comprises a new Poinsettia, botanically known as *Euphorbia pulcherrima*, and hereinafter referred to by the variety name 'EURZ0005'.

'EURZ0005' is a product of a planned breeding program. The new cultivar has bright bluish red bract color, relatively large inflorescences with slightly serrated bracts a little upright directed, dark green foliage, early flowering response, and medium to strong vigor with good branching.

'EURZ0005' results from an open pollination in a breeding program made in September 2011 in a greenhouse in Enkhuizen, The Netherlands. The female parent was a patented, proprietary plant of 'Fiselfi', described in U.S. Plant Pat. No. 13,736, with more serrated bracts when compared to 'EURZ0005'. The father plant is unknown.

These plants were multiplied separately and examined during next fall-winter flowering for uniformity and stability of the new combination of characteristics.

Horticultural examinations of plants grown from cuttings of the plant started in the fall to winter of 2012 Examinations continuing thereafter on a larger scale, have demonstrated that the combination of characteristics as herein disclosed for 'EURZ0005' are firmly fixed and are retained through successive generations of asexual reproduction.

BRIEF SUMMARY OF INVENTION

Horticultural examination of plants grown from cuttings of the plant initiated in April 2012, and continuing thereafter, has demonstrated that the combination of characteristics as herein disclosed for 'EURZ0005' are firmly fixed and are retained through successive generations of asexual reproduction.

'EURZ0005' has not been observed under all possible environmental conditions. The phenotype may vary significantly with variations in environment such as temperature, light intensity and day length.

Plant Breeder's Rights for this cultivar were applied for in Canada on Apr. 7, 2017, No. 17-9176 and in the European Union on Dec. 22, 2016, No. 2016/3239. 'EURZ0005' has not been made publicly available prior to the effective filing date of this application, notwithstanding any disclosure that may have been made less than one year prior to the effective filing date of this application by the inventor or another who obtained 'EURZ0005' directly from the inventor.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

The accompanying photographic drawing shows typical flower and foliage characteristics of 'EURZ0005' with colors being as true as possible with an illustration of this type. The photographic drawings show flowering potted plants of the new variety.

Figure 1:
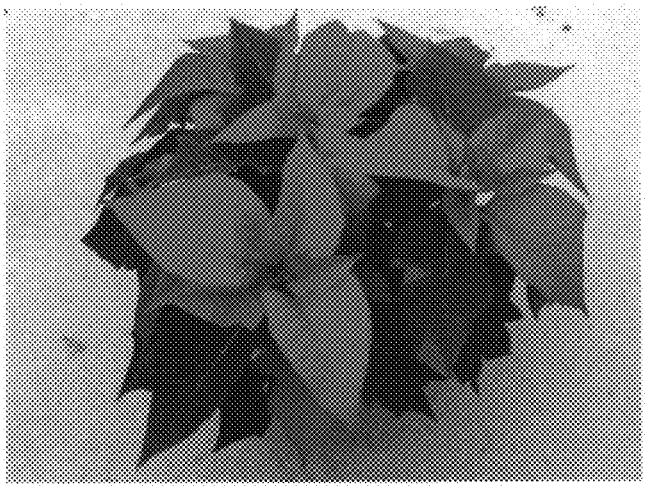
Figure 2:
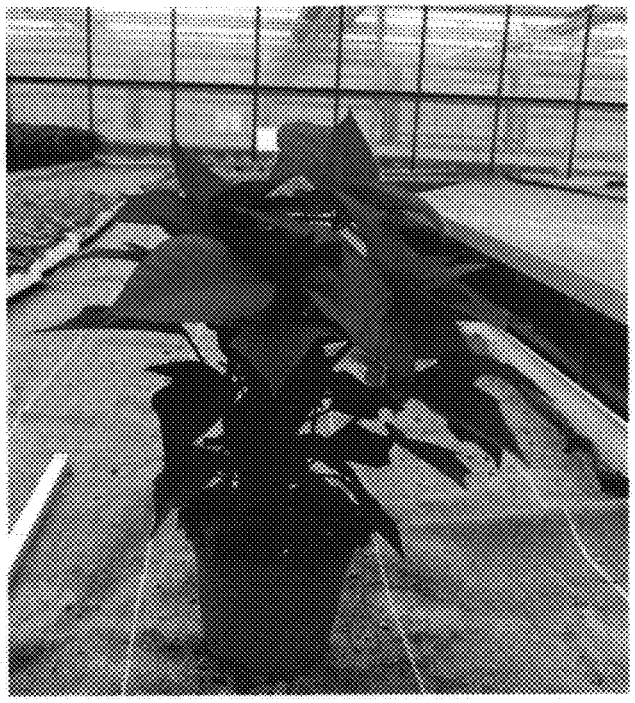

FIG. 1, taken on Nov. 27, 2016, shows a view of the bracts from the top of plant, on a plant about 21 weeks old;

FIG. 2, taken on Nov. 27, 2016, shows a side view of the same plant.

DETAILED BOTANICAL DESCRIPTION

The measurements were taken in Enkhuizen, the Netherlands in end November 2016 on 21 week old plants growing in a greenhouse. Culture of these plants had started in late June 2016 with planting rooted cuttings in 12 cm pots and terminal pinching about 3 weeks later. The plants were grown under natural day light in the fall (no black cloth to initiate earlier flowering) and at the moderately warm temperature of 18° C. for the bench heating. No use of PGR.

Color references are made to The Royal Horticultural Society Colour Chart (R.H.S.) 2001.

TABLE 1

DIFFERENCES BETWEEN THE NEW VARIETY 'EURZXXXX' AND A SIMILAR VARIETY

| | 'EURZ0005' | 'Fiselfi' |
|---|---|---|
| Shape of lobes on oldest bract: | Longer lobe with narrow tip in particular in cooler greenhouse (16° C.) | Wide short lobe |

Plant:

*Form, growth and habit.*—Shrub, with the branches slanting upright, good branching.

*Plant height (inflorescence included).*—23-26 cm.

*Plant width.*—30-33 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155B but whiter.

Foliage:

*Arrangement.*—Alternate, 5-8 leaves per branch.

*Immature, leaf color, upper surface.*—Approximately RHS 143A.

*Lower surface.*—RHS 144B.

*Mature, leaf color, upper surface.*—RHS 139A.

*Lower surface.*—RHS 138B.

*Length.*—13-18 cm.

*Width.*—5-10 cm.

*Shape.*—Ovate, with one or two lobes.

*Base shape.*—Truncate to obtuse.

*Apex shape.*—Acuminate.

*Margin.*—Entire; lobes, when present mostly rounded.

*Aspect.*—Leaf blades are horizontally or slightly downwards directed.

*Texture, upper surface.*—Smooth.

*Lower surface.*—Smooth, apart from the protruding veins.

*Color of veins, upper surface.*—RHS 53B or RHS 47A at the base, fading towards the leaf tip.

*Color of veins, lower surface.*—RHS 48A fading towards the leaf tip.

*Petiole color, upper surface.*—RHS 59A.

*Lower surface.*—RHS 53A.

*Length.*—5-6 cm.

*Diameter.*—0.3-0.4 cm.

*Aspect.*—Horizontally to slightly upward directed.

*Texture.*—Glabrous.

Stem:

*Quantity of main branches per plant.*—About 7-9.

*Color of stem.*—RHS 146A with stripes RHS 60A, fading to RHS 146C at the tip.

*Length of stem.*—13-17 cm.

*Diameter.*—0.5-0.7 cm.

*Length of internodes.*—0.5-3.5 cm.

*Texture.*—Glabrous.

*Color of peduncle.*—RHS 144B to RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically (opening of the stamen, shedding of pollen).*—Late November.

*Flowering, commercially (sufficiently colored bracts).*—Mid November, week 46.

*Flowering response time.*—About 7-7.5 weeks from equinox.

*Duration of flowering.*—Depends on light and environment, at least 4-6 weeks of 'shelf' life.

*Fragrance.*—Absent.

*Shape of inflorescence.*—Rosette-like whorl, star-shaped; bracts borne nearly horizontally to weakly funnel-shaped (slanting upright); tight center.

*Diameter of inflorescence.*—25-27 cm.

*Inflorescence, vertical diameter.*—4.5-9 cm.

*Number of completely colored bracts per inflorescence (sized over 2 cm).*—12-14.

*Single bract, shape.*—Ovate with relatively long, pointed tips, with lobes on lower bracts.

*Bract, apex.*—Acuminate.

*Bract, base.*—Weakly rounded.

*Single bract, length of blade.*—15 cm, younger bracts diminishing in size.

*Single bract, width of blade.*—8-10 cm.

*Bract color, upper side.*—RHS 47A.

*Bract color, lower side.*—RHS 53C.

*Vein color, upper surface.*—Indistinct, similar as bract blade on upper bracts, lower bracts RHS 60A.

*Vein color, lower surface.*—Approximately RHS 48B side veins.

*Texture.*—Weakly rugose, glabrous.

*Bract petiole color, upper surface.*—RHS 60A.

*Bract petiole color, lower surface.*—RHS 60A.

*Bract petiole, length.*—2-3 cm.

*Bract petiole diameter.*—0.2-0.3 cm.

Cyme (true inflorescence):

*Cyme, diameter.*—1.5 cm.

*Number of cyathia.*—5-10, borne in a tight cluster.

*Cyathium, shape.*—Ovate.

*Cyathium, diameter.*—0.3-0.4 cm.

*Cyathium, length.*—0.5-0.7 cm.

*Color.*—RHS 144A to RHS 144B, top is RHS 45A.

*Nectar cups.*—Usually one per cyathium.

*Nectur cup, width.*—0.3-0.4 cm.

*Nectar cup, color.*—RHS 17B to RHS 33B, a little reddish infusion may occur at the margin: RHS 34C.

Reproductive organs:

*Stamen (actually reduced male florets).*—Usually in a small bunch of 5 at the top of the cyathium.

*Shape.*—Strap-like.

*Filament length.*—0.4 cm.

*Filament color.*—RHS 46A to RHS 46B.

*Anther color.*—RHS 11A.

*Anther diameter.*—0.1 cm.

*Pollen quantity.*—Moderate (normal quantity).

*Pollen color*.—RHS 12A.

*Female flowers*.—Not yet observed.

*Fertility/seed set*.—Has not been observed on this plant.

Disease/pest resistance: Disease/pest resistance has not been observed on this plant.

What is claimed is:

1. A new and distinct variety of Poinsettia plant named 'EURZ0005', substantially as illustrated and described herein.

* * * * *